(12) United States Patent
Davey et al.

(10) Patent No.: US 12,249,411 B2
(45) Date of Patent: *Mar. 11, 2025

(54) PRESCRIPTION DISPENSING SYSTEM

(71) Applicants: Neil S. Davey, Gaithersburg, MD (US); Brendan Boyce Murphy, Bala Cynwyd, PA (US); Sonya R. Davey, Gaithersburg, MD (US); Haris Godil, Boyds, MD (US)

(72) Inventors: Neil S. Davey, Gaithersburg, MD (US); Brendan Boyce Murphy, Bala Cynwyd, PA (US); Sonya R. Davey, Gaithersburg, MD (US); Haris Godil, Boyds, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,174

(22) Filed: Oct. 23, 2023

(65) Prior Publication Data
US 2024/0047034 A1    Feb. 8, 2024

Related U.S. Application Data

(63) Continuation of application No. 17/550,240, filed on Dec. 14, 2021, now Pat. No. 11,848,087, which is a
(Continued)

(51) Int. Cl.
*G16H 20/13*  (2018.01)
*G06Q 10/087*  (2023.01)
*G06Q 10/1093*  (2023.01)

(52) U.S. Cl.
CPC .......... *G16H 20/13* (2018.01); *G06Q 10/087* (2013.01); *G06Q 10/1093* (2013.01)

(58) Field of Classification Search
CPC .... G16H 20/13; G16H 40/20; G07F 17/0092; G06Q 10/087; G06Q 10/1093
See application file for complete search history.

(56) References Cited

U.S. PATENT DOCUMENTS

| | | | |
|---|---|---|---|
| 6,711,460 B1 * | 3/2004 | Reese ................... | G16H 20/10 700/216 |
| 10,335,953 B2 * | 7/2019 | Davey ................... | B25J 11/009 |

(Continued)

*Primary Examiner* — Timothy R Waggoner
(74) *Attorney, Agent, or Firm* — Davé Law Group, LLC; Raj S. Davé

(57) ABSTRACT

A pharmacy automation system having a robot having a hardware device and a software for internal mapping to perform simultaneous localization and mapping (SLAM) is disclosed herein. The robot is configured to use the SLAM technique to carry out at least the following different interactions: the robot communicates autonomously with a physician or an assistant directly or via an intermediary; the robot interacts with an inventory of goods and browses the inventory of goods to determine if a prescribed medication is available in the pharmacy; if the prescribed medication is available in the pharmacy, the robot interacts with a medication dispenser, using the internal mapping to fill a container with the prescribed medication, and store the container; when a patient or a proxy arrives to pick up the prescribed medication, the robot checks and approves an identification of the patient or the proxy; and when the patient or proxy presents a prescription containing the prescribed medication, the robot retrieves the container with the prescribed medication and hands the container with the prescribed medication over to the patient or proxy.

20 Claims, 9 Drawing Sheets

Related U.S. Application Data continuation of application No. 16/458,654, filed on Jul. 1, 2019, now Pat. No. 11,200,979, which is a continuation of application No. 15/824,471, filed on Nov. 28, 2017, now Pat. No. 10,335,953, which is a continuation of application No. 15/589,489, filed on May 8, 2017, now Pat. No. 9,827,680, which is a continuation of application No. 14/706,982, filed on May 8, 2015, now Pat. No. 9,643,320, which is a continuation of application No. 13/584,862, filed on Aug. 14, 2012, now Pat. No. 9,043,012.

(60) Provisional application No. 61/528,566, filed on Aug. 29, 2011.

(56) References Cited

U.S. PATENT DOCUMENTS

| | | | |
|---|---|---|---|
| 11,848,087 B2 * | 12/2023 | Davey | G16H 10/60 |
| 2006/0116905 A1 * | 6/2006 | Yered | G16H 40/67 |
| | | | 705/2 |
| 2007/0192910 A1 * | 8/2007 | Vu | G05D 1/0246 |
| | | | 901/1 |
| 2008/0147518 A1 * | 6/2008 | Haider | G16H 70/40 |
| | | | 705/28 |

* cited by examiner

ROBOT STORAGE AND RETRIEVAL ARCHITECTURE
When the drug requested by the Doctor is available ...
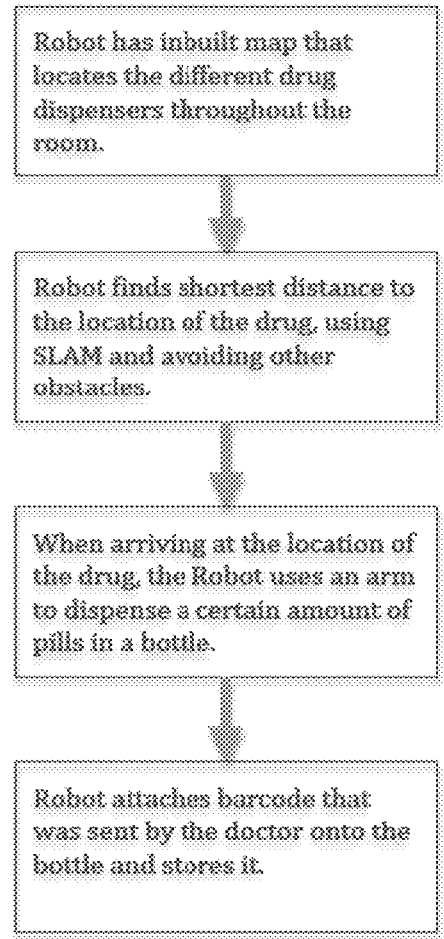
When the client arrives with prescription and the barcode is scanned...
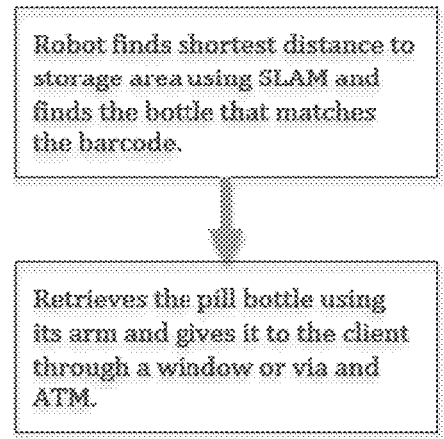
FIG.5

Verifying people/mailboxes to where the medications will be delivered

Example of Delivery System Matrix/Verification Checklist per Client:

| Client Name | Delivery Location Address | Modes of Delivery (with Names) | Biometric Checkbox |
|---|---|---|---|
| John Smith | 2212 Red Drive, Gaithersburg, MD 20878 | Self pick-up: John Smith | ☐ Fingerprint<br>☐ Signature<br>☐ Pupil analysis<br>☐ Other* |
| | | Representative pick-up: Sarah Lane | ☐ Fingerprint<br>☐ Signature<br>☐ Pupil analysis<br>☐ Other* |
| | | Representative pick-up: Lauren Front | ☐ Fingerprint<br>☐ Signature<br>☐ Pupil analysis<br>☐ Other* |
| | 6619 Tomato Lane Miami, FL 19203 | Representative pick-up: Donna Brown | ☐ Fingerprint<br>☐ Signature<br>☐ Pupil analysis<br>☐ Other* |
| | | Representative pick-up: Sara Trident<br>Mailbox pick-up: Secured mailbox at the door | ☐ Fingerprint<br>☐ Signature<br>☐ Pupil analysis<br>☐ Other*<br>☐ Secure mailbox**<br>☐ Mailbox needs key + password to open |
| | 7708 Tree Drive Las Vegas, NV 14420 | Self pick-up: John Smith | ☐ Fingerprint<br>☐ Signature<br>☐ Pupil analysis<br>☐ Other* |
| | | EMPTY CELL. NO ADDITIONAL DELIVERY MODE. | EMPTY CELL |
| | | EMPTY CELL. NO ADDITIONAL DELIVERY MODE. | EMPTY CELL |

Once a mode of delivery has been verified, he/she/it will receive a Medical Card Pick-up for the client. For the mailbox, the Medical Pick-up card will be taped to the inside of the mailbox.

*FIG. 8*

PRESCRIPTION DISPENSING SYSTEM

RELATED APPLICATIONS

The present application is a continuation application of U.S. patent application Ser. No. 17/550,240, filed Dec. 14, 2021, which is a continuation application of U.S. patent application Ser. No. 16/458,654, filed Jul. 1, 2019, now U.S. Pat. No. 11,200,979, issued Dec. 14, 2021, which is a continuation application of U.S. patent application Ser. No. 15/824,471, filed Nov. 28, 2017, now U.S. Pat. No. 10,335,953, issued Jul. 2, 2019, which is a continuation application of, and claims priority from, U.S. patent application Ser. No. 15/589,489, filed May 8, 2017, now U.S. Pat. No. 9,827,680, issued Nov. 28, 2017, which is a continuation application of U.S. patent application Ser. No. 14/706,982, filed May 8, 2015, now U.S. Pat. No. 9,643,320, issued May 9, 2017, which is a continuation of U.S. patent application Ser. No. 13/584,862, filed Aug. 14, 2012, now U.S. Pat. No. 9,043,012, issued May 26, 2015, entitled, "PHARMACY AUTOMATION USING AUTONOMOUS ROBOT", and said U.S. patent application Ser. No. 13/584,862 claims the benefit of priority to U.S. Provisional Patent Application 61/528,566, filed Aug. 29, 2011. Each of these applications are incorporated herein by reference in their entireties.

All publications, patents, and patent applications cited in this specification are hereby incorporated by reference in their entirety.

FIELD OF THE INVENTION

Embodiments of the present invention generally relate to a method and system for providing an improved approach for automating pharmacies using robotics and artificial intelligence (AI).

BACKGROUND OF THE INVENTION

A robot is a mechanical or virtual intelligent agent that can perform tasks automatically or with guidance, typically by remote control. An autonomous robot (also referred to as automaton) is a robot that can perform desired tasks in structured or unstructured environments without continuous human guidance. In today's world, robots may be used in many sectors (or applications) such as the medical sector, the banking sector, the transportation sector, the military sector, etc. More particularly, robots may be used to automate the pharmaceutical sector. For example, autonomous robots may be configured in such a way as to make prescription drug distribution more efficient and effective, without requiring any human intervention.

Robots need to be able to create a map using map-making algorithms that accurately displays their environment, in order to be effective in their application. Maps display what robots see; and therefore, it is vital that these maps are as accurate as possible, because they lead to more practical applications of these types of robots.

Currently available technologies use dead reckoning as a mapping method in navigation of robots, which calculates the current position of the robot by using a previously determined position. However, this method does not produce accurate maps because of wheel slips or skidding that would not allow rotary encoders in the wheels to produce proper results. What is needed is an accurate location service which may be applied to automating the pharmaceutical and medical sectors, and which overcomes the limitations exhibited by current methods.

Simultaneous localization and mapping (SLAM) is such a technique. SLAM is a technique used by robots and autonomous vehicles to build up a map within an unknown environment (without a priori knowledge), or to update a map within a known environment (with a priori knowledge from a given map, usually given by laser data), while at the same time keeping track of their current location. With SLAM, robots can be used extensively to help the public in the pharmaceutical sector.

U.S. Pat. No. 6,711,460, which is incorporated herein in its entirety by reference, discloses a pharmaceutical system and method in which pharmaceutical care is provided via a robot by a remote professional serving multiple pharmacies.

Every year in the United States, an estimated 30 million pharmacy dispensing errors occur according to the information on the website http://www.youhaverights.com/. These types of mistakes result in an estimated 7,000 patient deaths and thousands more serious complications each year. Approximately one in every 1,000 prescriptions delivered nationwide has an error, according to the National Patient Safety Foundation, a nonprofit organization working to improve patient safety. Some pharmacy errors are harmless and result in no injury to the patient. However, in many cases, mistakes result in the wrong medication or dosage being given to the patient. Patients have died or suffered life-threatening injuries when a pharmacy employee mistook one drug for another with a similar name, misread a physician's or assistant's handwriting, or dispensed the incorrect dosage to the patient.

Many pharmacy errors are blamed on overworked pharmacists and pharmacy technicians who are under pressure as workloads become increasingly demanding. Being pressed to fill hundreds of prescriptions every day decreases the amount of time that pharmacists and their technicians devote to filling each prescription.

The most common types of pharmacy and dispensing errors include:
  Dispensing the wrong medication
  Dispensing the incorrect dosage
  Failure by a pharmacist or pharmacy technician to give consumers instructions for taking the medication Another type of pharmacy error involves the incorrect preparation and/or delivery of intravenous drugs to hospital patients. Intravenous solutions prepared at pharmacies may contain the wrong drug or incorrect dosage of the proper drug. Also, nurses and other hospital personnel may make mistakes in entering data into the computerized machines used to administer the intravenous solutions to patients, resulting in death and serious injuries.

Therefore, there is a need for robotically assisted pharmacies to dispense medication to eliminate or substantially minimize human errors.

SUMMARY

An embodiment relates to a pharmacy automation system comprising a robot comprising a hardware device and a software for internal mapping to perform simultaneous localization and mapping (SLAM), wherein the robot is configured to use the SLAM technique to carry out at least the following different interactions: the robot communicates autonomously with a physician (also referred herein as doctor) or an assistant directly or via an intermediary; the robot interacts with an inventory of goods and browses the inventory of goods to determine if a prescribed medication is available in the pharmacy; if the prescribed medication is available in the pharmacy, the robot interacts with a medication dispenser, using the internal mapping to fill a container with the prescribed medication, and store the container; when a patient or a proxy arrives to pick up the prescribed medication, the robot checks and approves an identification of the patient or the proxy; and when the patient or proxy presents a prescription containing the prescribed medication, the robot retrieves the container with the prescribed medication and hands the container with the prescribed medication over to the patient or proxy.

Another embodiment relates to a tangible non-transitory computer readable medium comprising computer executable instructions that, when executed by one or more processors, cause the one or more processors to conduct pharmacy automation, comprising robotically assisting a patient or a proxy using a robot to obtain a prescribed medication from a pharmacy, wherein the robot is configured to carry out at least the following different interactions: if the prescribed medication is available in the pharmacy, the robot interacts with a medication dispenser, using internal mapping to fill a container with the prescribed medication, and store the container; when the patient or the proxy arrives to pick up the prescribed medication, the robot checks and approves an identification of the patient or the proxy; and when the patient or proxy presents a prescription containing the prescribed medication, the robot retrieves the container with the prescribed medication and hands the container with the prescribed medication over to the patient or proxy.

Yet another embodiment relates to a method for conducting pharmaceutical automation, comprising assisting one or more customers of one or more pharmacies using one or more autonomous robots for storage and retrieval of prescription medications, which includes prescription drugs, deposited in a medical cache, wherein, during said storage and retrieval of drugs by the robot: (a) each of the plurality of the customers maintains his or her identity in privacy within a customer database, accessible by the robot, making a prescription medication easier to locate, for example, based on his or her previous recorded conditions and/or doctor's prescription; (b) the plurality of the customers are able to retrieve prescription drugs simultaneously, and in different locations; and (c) identification of each of the plurality of the customers is verified with either one, or a combination of a physician's or an assistant's prescription note, patient records, biometric data, physical keys, passwords, an identification card and a medical card.

BRIEF DESCRIPTION OF THE DRAWINGS

FIG. 5—Retrieval and storage of goods by the robot.
FIG. 8—A scheme for verifying people/mailboxes to where goods will be delivered.

DETAILED DESCRIPTION

Figure 1:
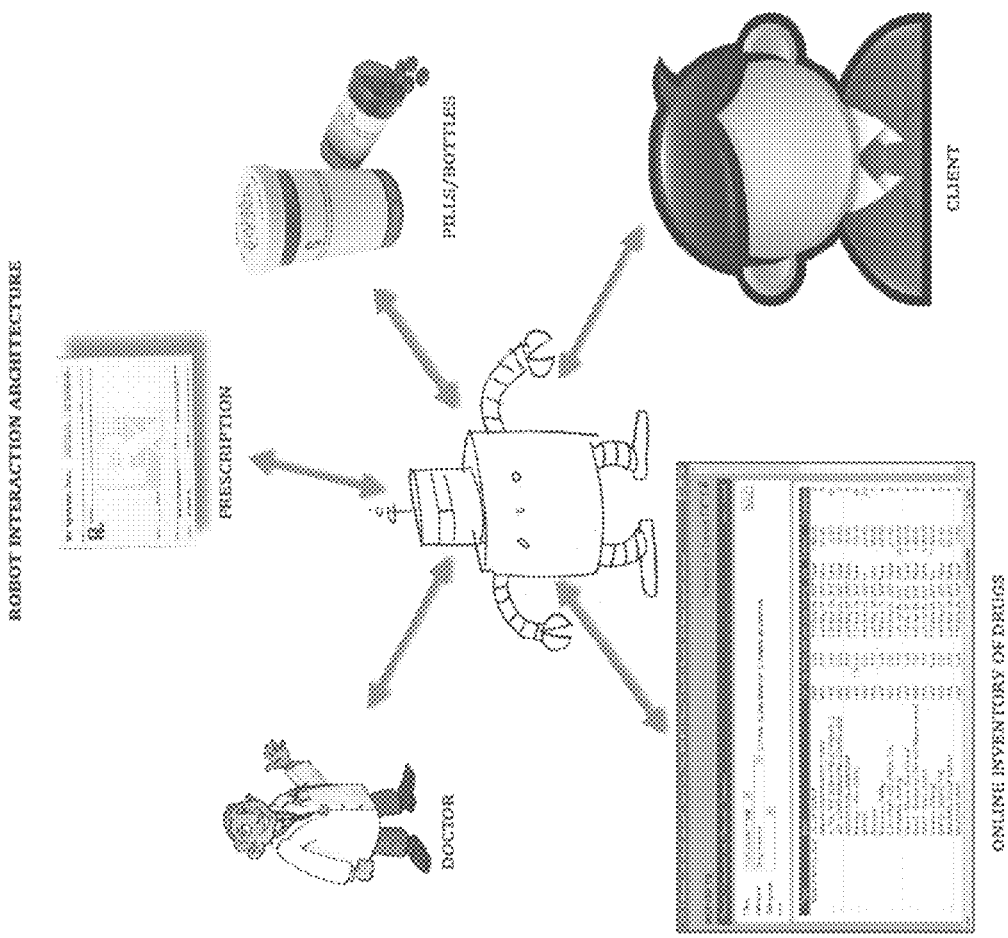
FIG. 1—General robot interactions.
Figure 2:
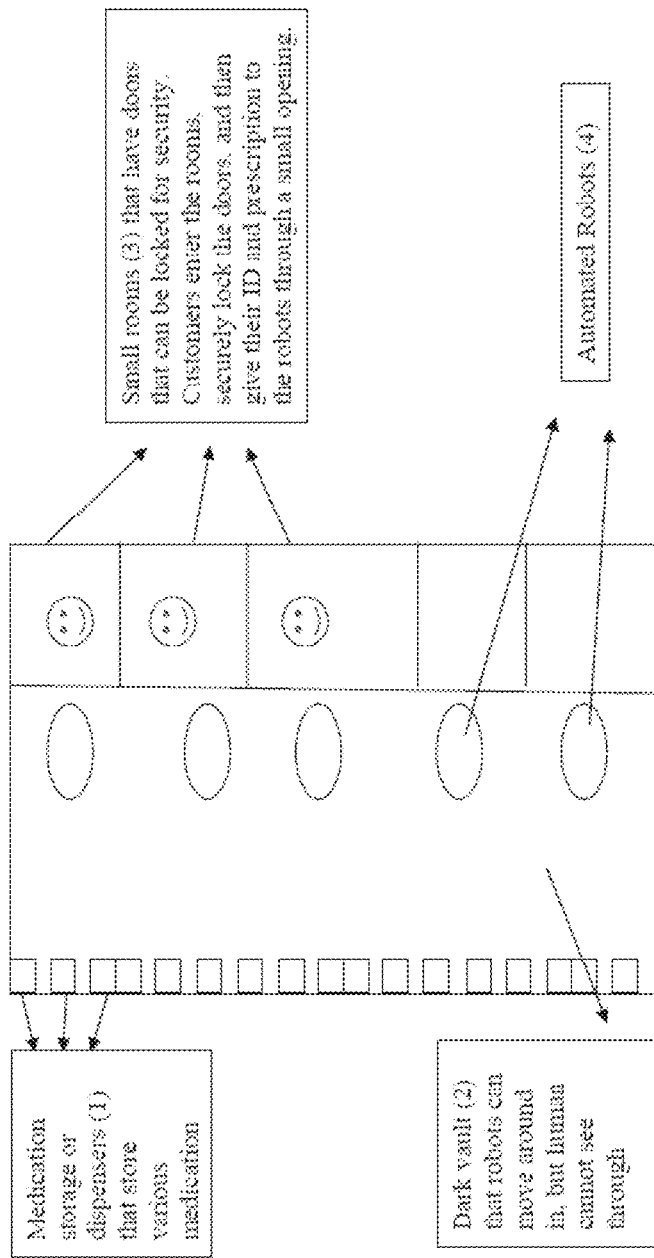
FIG. 2—Architecture of the pharmacy area.
Figure 3:
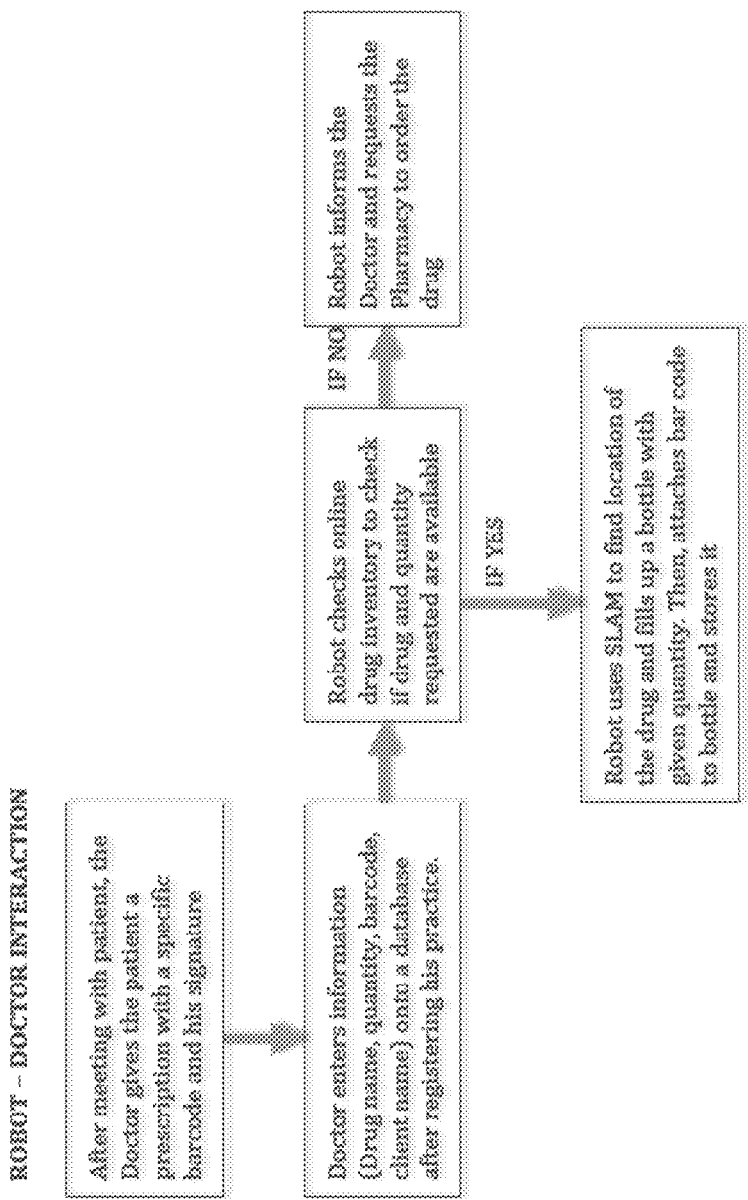
FIG. 3—Robot's interactions with medical professionals (doctors or assistants including nurses).
Figure 4:
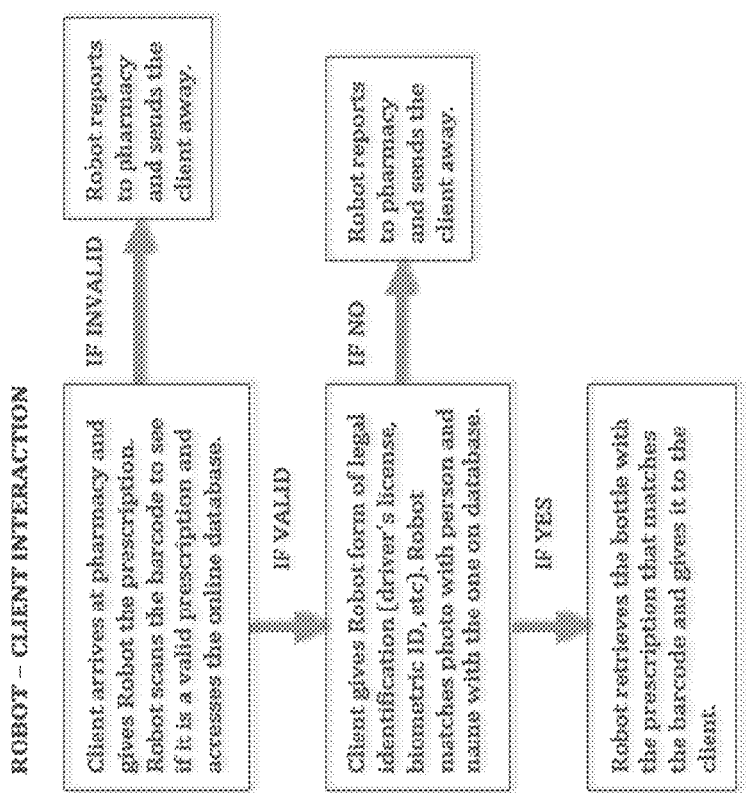
FIG. 4—Robot's interactions with customers (patients).

Maps are used to determine a location within an environment and to depict an environment for planning and navigation; they support the assessment of actual location by recording information obtained from a form of perception and comparing it to a current set of perceptions. The benefit of a map in aiding the assessment of a location increases as the precision and quality of the current perceptions decrease. Maps generally represent the state at the time that the map is drawn; this is not necessarily consistent with the state of the environment at the time the map is used.

The complexity of the technical processes of locating and mapping under conditions of errors and noise do not allow for a coherent solution of both tasks. Simultaneous localization and mapping (SLAM) is a concept that binds these processes in a loop and therefore support the continuity of both aspect in separated processes; iterative feedback from one process to the other enhances the results of both consecutive steps.

Mapping is the problem of integrating the information gathered by a set of sensors into a consistent model and depicting that information as a given representation. It can be described by the first characteristic question, What does the world look like? Central aspects in mapping are the representation of the environment and the interpretation of sensor data.

In contrast to this, localization is the problem of estimating the place (and pose) of the robot relative to a map; in other words, the robot has to answer the second characteristic question, Where am I? Typically, solutions comprise tracking, where the initial place of the robot is known, and global localization, in which no or just some a priori knowledge of the environmental characteristics of the starting position is given.

SLAM is therefore defined as the problem of building a model leading to a new map, or repetitively improving an existing map, while at the same time localizing the robot within that map. In practice, the answers to the two characteristic questions cannot be delivered independently of each other.

Before a robot can contribute to answering the question of what the environment looks like, given a set of observations, it needs to know e.g.: the robot's own kinematics; which qualities the autonomous acquisition of information has, and; from which sources additional supporting observations have been made. It is a complex task to estimate the robot's current location without a map or without a directional reference. Here, the location is just the position of the robot or might include, as well, its orientation.

SLAM can be thought of as a chicken or egg problem: An unbiased map is needed for localization while an accurate pose estimate is needed to build that map. This is the starting condition for iterative mathematical solution strategies.

The answering of the two characteristic questions is not as straightforward as it might sound due to inherent uncertainties in discerning the robot's relative movement from its various sensors. Generally, due to the budget of noise in a technical environment, SLAM is not served with just compact solutions, but with a bunch of physical concepts contributing to results. If at the next iteration of map building the measured distance and direction traveled has a budget of inaccuracies, driven by limited inherent precision of sensors and additional ambient noise, then any features being added to the map would contain corresponding errors. Over time and motion, locating and mapping errors build cumulatively, grossly distorting the map and therefore the robot's ability to determine (know) its actual location and heading with sufficient accuracy.

Different aspects of SLAM include the following:
(1) Mapping, i.e., the process of creating geometrically consistent maps of the environment.
(2) Sensing, i.e., using several different types of sensors to acquire data with statistically independent errors. The sensors could be optical sensors that may be one-dimensional (single beam) or 2D-(sweeping) laser rangefinders, 3D Flash LIDAR, 2D or 3D sonar sensors and one or more 2D cameras. For VSLAM (visual SLAM), the sensors could be visual (camera) sensors. The sensors could also be quasi-optical wireless sensors ranging for multi-lateration (RTLS) or multi-angulation in conjunction with SLAM. A special kind of SLAM for human pedestrians could use a shoe mounted inertial measurement unit as the main sensor and relies on the fact that pedestrians are able to avoid walls. This approach called FootSLAM can be used to automatically build floor plans of buildings that can then be used by an indoor positioning system Locating: The results from sensing could be fed to the algorithms for locating. According to propositions of geometry, any sensing could include at least one lateration (a navigation technique based on the measurement of the difference in distance to two or more stations at known locations that broadcast signals at known times) and (n+1) determining equations for an n-dimensional problem In addition, there could be some additional a priori knowledge about orienting the results versus absolute or relative systems of coordinates with rotation and mirroring.
(3) Modeling: Contribution to mapping may work in 2D modeling and respective representation or in 3D modeling and 2D projective representation as well. As a part of the model, the kinematics of the robot could be included, to improve estimates of sensing under conditions of inherent and ambient noise. The dynamic model balances the contributions from various sensors, various partial error models and finally comprises in a sharp virtual depiction as a map with the location and heading of the robot as some cloud of probability. Mapping is the final depicting of such model; the map is either such depiction or the abstract term for the model.

Embodiments herein, as disclosed in U.S. Pat. No. 6,711,460, which is incorporated herein in its entirety by reference, include an exemplary embodiment which permits a single pharmacist or other professional who can deliver prescription drugs, who would be referred to herein as a "pharmacist," to simultaneously serve several individual pharmacies. In an exemplary embodiment a pharmacist would generally work at a location that is remote from most or all of the individual pharmacies being served. In order to accomplish this, the remote pharmacist would be in direct computer connection, over a network, with each of the individual pharmacies being served. Through this network, the pharmacist would be connected with user service stations, drug vaults, and a customer service computer located within each individual pharmacy. The connection would include CCTV connections to each of these locations within the individual pharmacies, permitting the pharmacist to observe a robot or other device preparing prescriptions in the drug retrieval vault and in the drug compounding vault, and to communicate directly with customers and local technicians.

In an exemplary embodiment, the pharmacist's computer is adapted to permit the pharmacist to control the robots in one or more drug vaults from a remote location. The remote pharmacist is in interactive communication with the robots in the individual pharmacies as the robots prepare the items that are to be dispensed to each customer.

In an exemplary embodiment of a pharmacy the remote pharmacist would have access to one or more processing and data storage devices containing individual patient histories for the group of pharmacies he or she serves, general information about the drugs which may be dispensed, the rules that apply to the various insurance plans accepted by each pharmacy, persons registered to prescribe medications, and the items stocked in each location. These data storage and processing devices may be in the same physical location as the remote pharmacist, or the pharmacist may be connected to these devices through one or more networks. The network used in an exemplary embodiment is separated from any external network by a pharmacist's computer which includes a firewall, or other means to prevent unauthorized access.

Each of the individual pharmacies served by a remote pharmacist is equipped with an automated drug preparation and compounding area, and may have one or more self-service customer terminals through which the patient can access pharmaceutical services. The individual pharmacies may also have a traditional customer service area, which is staffed by an individual. A computer in each local pharmacy controls and coordinates the network within that pharmacy. It includes a firewall or other means to prevent unauthorized access. Each of the individual pharmacies is connected to a remote pharmacist via a computer network system.

Customer terminals, if they are part of an embodiment of an individual pharmacy, may be walk-up terminals inside the store or drive-through terminals on the outside of the pharmacy. Customer terminals include a way for the patient to submit a prescription to be filled, to communicate with the pharmacist, to pay for the prescription, and to take delivery of the prescription. These functions may all be contained in a single customer terminal or split between two or more customer terminals. Some of the functions of a customer terminal would be performed using (1) dedicated input devices, such as a card reader, a prescription scanner, or a bar code reader; (2) dedicated output devices, such as printers adapted to print drug information sheets and receipts; and (3) interactive communication devices, such as Closed Circuit Television ("CCTV"), and intranet or internet connections. Most customer terminals would also include access to a pneumatic delivery system, which connects the parts of the local pharmacy so that objects can be sent between them.

An exemplary embodiment of the drug preparation area would generally include two vaults in which robots prepare the items requested. An exemplary embodiment of the first vault would include storage cells around the walls of the vault. These storage cells would contain the medications or medication components most commonly used in a particular pharmacy, and other items that could be dispensed through the pharmacy. Such an embodiment would also include a preparation area that includes various automated counting or measuring devices.

In the exemplary embodiment a relatively simple robot is located within the drug retrieval vault. The robot is adapted to perform one or more tasks necessary to prepare simple pharmaceutical orders. The robot is also adapted to perform one or more tasks necessary to deliver the raw ingredients for more complicated pharmaceutical orders to the drug compounding vault. Finally, the robot is adapted to package and deliver the prepared pharmaceutical order to the customer. Actions of the robot could be autonomous by the robot or optionally directed by a pharmacist from a remote location.

In addition, an exemplary embodiment of a pharmacy using the system and method of this invention includes a drug compounding vault. This vault is used to prepare medications which cannot be delivered to the patient in the form in which they are stored in the pharmacy. The compounding performed may be minor, such as mixing water with a powder just before the medication is delivered to the patient. It may also be more complex, such as preparing an individualized medication from several ingredients.

An exemplary embodiment of a drug compounding vault includes the various devices that a pharmacist would need to compound drugs. The exemplary drug compounding vault is in direct connection with the drug preparation vault via a pneumatic delivery tube. An exemplary embodiment may also include a sophisticated medical robot, equipped with various sensor devices similar to those used in surgical robots.

An exemplary robot in an exemplary drug compounding vault is adapted to perform complex manipulations with raw ingredients, using traditional compounding tools, at the direction of a remote pharmacist. The robot is also adapted to retrieve ingredients sent to it by the robot in the drug retrieval vault and to return the compounded pharmaceutical item to the robot in the drug retrieval vault.

An exemplary embodiment of a pharmacy may also include a traditional customer service desk at which an individual may speak directly with a technician. In an exemplary embodiment of a system including this feature, the technician would gather the information from the patient, and transmit it to a remote pharmacist and/or the robot, using devices that may be similar to those available to the customer at a customer terminal. The robot would prepare and deliver the prescription medication to the customer while the remote pharmacist could provide counseling to the customer. The look and feel of the interaction at a customer service desk would generally be similar to the look and feel of a traditional pharmacy interaction, with the exception that patients would receive counseling over the CCTV rather than face-to-face.

In addition, in an exemplary embodiment of a pharmacy using this method, a prescriber or a customer may use the telephone to request pharmaceutical care. Depending on the laws of the state, the technician at the service desk would either transmit the prescription in the form of an audio or digital recording to the remote pharmacist or would enter the information into the pharmacy computer which would then transmit it in facsimile form to the remote pharmacist. The system may also be configured to accept direct computer-to-computer transmissions of prescriptions from individual prescribers.

ROBOT INTERACTION ARCHITECTURE (FIG. 1)

As shown in FIG. 1, the robot could use artificial intelligence (AI) and SLAM to interact with five different things. First, the robot would communicate autonomously with doctors via an online database. This database would contain a detailed list of doctors and patients that are registered as part of the particular pharmacy. The robot would then interact with an online inventory of goods, which it can browse to determine if the doctor's requests can be fulfilled. If the requests can be completed, the robot would have another interaction, using its internal mapping to fill bottles with specific pills, and then store the bottles. Finally, when a customer arrives, he/she would first get his/her identification approved by the robot. Next, the same customer would present a prescription note indicating a valid doctor's practice and the drugs that need to be dispensed. The robot would then retrieve the bottle that matches the specifications and hand them over to the customer.

In one embodiment, the patient could have a medical card with a build-in memory chip and for identifying purposes, the automaton would use the medical card with a built-in memory chip along with some other form of an IP card. For example, the physician or the assistant could insert the medical card and another personal ID card (e.g. a driver's license or credit card) with a code, such as a barcode, into a read/write device attached to the in-network doctor's computer. The prescription would be downloaded into the memory chip of the medical card. Also, a feature such as a barcode on the personal ID card would also be downloaded into the memory chip of the medical card, and would be associated with the prescription saved in the memory chip. If a proxy is going to get the prescription filled, then the ID card of the proxy would also be associated with the prescription. Then, when the patient or the proxy goes to the pharmacy, he/she would give both the personal ID card and the medical card to the pharmacy automaton, which would then in turn authenticate the patient or proxy, and the dispense the prescribed drug to the patient or proxy.

To move around inside the pharmacy, after an inbuilt map is created that identifies the locations of specific drugs, the robots would have to find the shortest path to their destination to work most efficiently. To actually do this, the robot could be using Simultaneous Localization and Mapping (SLAM). The Robot Operating System, or ROS (a robot software geared towards Linux systems for open source collaboration of robotic software), contains multiple SLAM, or Simultaneous Localization and Mapping, implementations. After doing some experiments, data that was presented showed that Gmapping, an implementation of SLAM, is far more accurate than other mapping algorithms such as Dead Reckoning, a mapping method in navigation that calculates current position by using a previously determined position. With currently available mobile robots, rotary wheel encoders determine the position of the robot. The main problem that arises with a two-wheel drive train is that the robot's wheels tend to frequently slip or skid, especially during turning, causing the encoders to return larger values than what they should. When encoder data is mapped, it is quite inaccurate, as no measures are taken to properly correct the slips and skids that have occurred. Using dead reckoning can lead to disasters in the pharmacy, as robots may pick up incorrect prescriptions by mistake.

On the other hand, SLAM builds a map whilst in an unknown environment, and still keeps track of the current position. SLAM utilizes both rotary encoders and lasers to create a more accurate map. Rotary encoders are used to keep track of the current location, and laser scans from a laser measurement technology device made by SICK are used to correct the map when the wheels slip or skid. The laser measurement technology device can be used for a wide range of applications. The device, which detects both two-dimensional and multi-dimensional contour data, can process information either externally or in the sensor itself. Since the encoders and the laser measurement device are working in unison, they are configured to create a more accurate map. SLAM was proven to be far more accurate after experimentation by one of the inventors. For this reason, it would be used as the primary software for robotic mapping.

In addition to the information downloaded into the memory card above mentioned, the patient's medical information would be uploaded into a cloud network. The password to access the information on the cloud would also be downloaded into the memory chip of the medical card. When the pharmacy fills the prescription, and when the pharmacy delivers the prescription to the patient, the automaton would access the cloud, and double-check if the information on the cloud matches the information in the memory chip. The pharmacy would also take a picture of the person who has come to the pharmacy to get the prescription medicine. Once the pharmacy has authenticated the patient or proxy, and dispenses the drug to the patient or proxy, the pharmacy would upload this information, plus the photograph of the person who came to the pharmacy, on to the cloud. This information, in turn, would be transmitted to the physician or the assistant from the cloud. The physician or the assistant's office would thus know if the patient has obtained his/her medication, and whether the medication was picked up from the pharmacy by the patient or the proxy.

Unlike today's pharmacies, this automated pharmacy using intelligent mobile robots could give multiple people access to their medication dispensers with increase privacy and security. The rooms that each individual is in could be locked, preventing the chance of a robbery. There could be multiple identity checks done by the robot, and this process could be fast and efficient due to the fact that there are multiple robots.

ARCHITECTURE OF THE PHARMACY AREA (FIG. 2)

An embodiment relates to the actual architecture of the pharmacy area. As shown in an exemplary schematic in FIG. 1, customers can enter the pharmacy and choose one of the multiple rooms. Each of these rooms is secure and can be locked from the inside. These smaller rooms are there so that customers can privately and safely give their keys and biometric information to the autonomous robots without others watching. It protects customers from being attacked by thieves and allows them to privately take out their medications. In addition, the vault where the various medication dispensers could be contained could be dark without any lights and maintained at a temperature, for example, in refrigerated conditions, to prevent deterioration of the medication during shelf life. Because of this, the robots could be able to move around in darkness and need not rely on the light to move around. Another advantage of having multiple rooms is that multiple people can access their medications and make use of the robots simultaneously. Of course, the number of rooms could vary according to the area given for the pharmacy. While optionally there could be different number of robots than the number of customer rooms, in another embodiment there could be the same number of robots as there are customer rooms. This way, multiple customers can make use of the robots to get their medications at the same time. Although it may be expensive to have so many robots, it could make a more efficient pharmacy and end up creating greater income. The extensive security checks done by the robots and the certainty of being given the correct medication could also encourage more customers to come to this pharmacy over another.

ROBOT—DOCTOR INTERACTION (FIG. 3)

A customer goes to his/her doctor's office, and, after examination, the physician or the assistant gives the patient a prescription, which is authenticated by a specific barcode and the physician's or the assistant's signature.

After meeting with and prescribing the patient, the doctor enters the prescription and customer information into his registered practice's database, which is accessible to the in-network pharmaceutical automatons. The information the doctor includes in the database entry are customer name and file, the barcode that authenticates the patient's prescription, the drug name itself, and the quantity, flavor and nature of the drug prescribed. ("Quantity" corresponds to amount. "Flavor" is an attribute that would become important if and when dealing with, say, children's prescription drugs; cherry, grape, apple, etc. would all be available flavors, and each would be identified and represented differently via the prescription barcode. Regarding the drug's "nature", pills as well as liquids would be accessible in the automation pharmacy, and they would be stored in separate compartments in the pharmacy itself, as well as identified separately by the pharmaceutical automaton according to their specific barcodes.)

All of the information provided by the doctor could also downloaded on to a medical card with a built-in memory chip, which constitutes the prescription. In addition to the medical card, all the information provided by the doctor could be uploaded to the cloud network of the in-network doctor's specific practice.

The in-network automatons are notified immediately of the prescription, as soon as the doctor finishes entering the data.

The robots check the online inventory of drugs for the drug prescribed to find (1) if the drug is in stock, and (2) if the quantity, flavor and nature of the drug requested is available in stock. From this point, there are a few possible circumstances:

a. If the requested drug is not in stock, or if the drug is in stock but not of the quantity, flavor and nature requested, the robot may inform the doctor, and simultaneously send a drug-creation request to an in-network pharmacy from which to order the drug.

i. When the robot informs the doctor of the absence of the prescribed drug, the doctor may decide to prescribe the patient with a different drug (different in quantity, flavor, nature, or some combination of the three), but which has similar characteristics to the original drug prescribed. If this is the case, the automaton would take the prescription change into account by searching its records for the newly prescribed drug. However, the request to the pharmacy for the original drug requested would still be sent, in case of future requests for that same specific drug.

b. If the requested drug is in stock, the robot uses SLAM to find the locations of both a pill bottle and the drug itself, and then fills up the bottle with the prescribed drug. Then, the automaton attaches a barcode to the bottle that corresponds to the barcode given to the customer on the doctor's prescription and stores the prescription until the customer comes to retrieve it.

ROBOT—CUSTOMER INTERACTION (FIG. 4)

Provided the drug is in stock when the customer arrives at the automation pharmacy, he/she would give the robot the prescription note given by the doctor. The robot would confirm that the barcode is from a registered doctor's office by attempting to access the customer's file with it. The dent's file would be available to the robot via the cloud network.

There are two possibilities from this point:
a. If the prescription is invalid, the robot would report the incident to the in-network pharmacy, to the doctor's office, and to the local law enforcement, and then send the customer away.
b. If the prescription is valid, the robot would proceed with the transaction by asking for some form of valid identification.

After being give some form of legal personal identification (i.e., driver's license, biometric ID, etc.), the robot would scan the license or other form of identification. If the names on the database and ID card match, the robot checks to make sure that the photo on the identification matches the image of the customer. The robot's basis for identification is the cloud network entry provided by the doctor. A person would not be able to trick the robot by simply stealing someone's prescription, as the barcode on the prescription pulls up a customer file on the database, which could match the name on the ID card. In addition, a person would not be able to trick the robot by stealing someone's prescription and ID card, as the customer's photo would be taken by the robot and matched to that of the identification card. The robot would also have special camera sensors to ensure that a person would not just hold up a photo of another customer whose drugs have to be picked up after stealing his/her prescription note and ID card. In addition, a barcode can only be used once to pick up medications. Once a customer gets his/her medications from the pharmacy, the person would not be able to use the prescription again or make copies of the barcode to try and get more drugs illegally, as the prescription would be deleted from the database. This prevents the abuse of pharmaceutical drugs.

If, however, the customer is too sick, young or disabled, and unable to pick up his/her own medications, the doctor can enter on the database the name of another person, who would be a proxy and pick up the medication for the ill customer. The doctor would also ensure that the proxy's name is mentioned on the prescription note. In this case, the robot would scan the proxy's identification card after scanning the prescription note's bar code. The name could match what is on the database as well as what is on the prescription note. In addition, the proxy's photo would be taken and compared to the photo given on the identification card.

From this point, two possibilities arise again:
a. If the identification of the customer does not match the records on file or the photo, the robot reports the incident to the in-network pharmacy, to the doctor's office, and to the local law enforcement, and then sends the customer away.
b. If the identification does match, the robot would proceed with the transaction.

After confirming validity of both the prescription and the customer, the robot would retrieve the pill bottle it stored earlier, which prescription has a barcode that matches the barcode on the doctor's note, and would give the bottle to the patient.

ROBOT RETRIEVAL AND STORAGE ARCHITECTURE (FIG. 5)

One possibility is that the drug requested by the doctor is in stock. In this case, the retrieval and storage could be as follows. The robot has an inbuilt SLAM technique map, which locates the different drug dispensers throughout the pharmaceutical storage room, and allows the robot to "see" where the specific prescription drug is located, according to the drug's flavor and nature. The robot finds the shortest distance to the location of the drug and its dispenser, and then again uses SLAM to move and avoid possible obstacles. Upon arriving at the location of the drug and its dispenser, the robot uses an arm to retrieve a pill bottle and place it beneath the drug dispenser; the robot then uses another arm to dispense the requested amount of prescription drug (pills or liquids) into the bottle placed beneath. When the pill bottle is full, the robot uses one of its arms to retrieve a lid and seals the prescription bottle; then, the robot attaches a barcode to the pill bottle, which barcode is identical to the barcode on the doctor's note being carried by the customer. The robot then uses SLAM to move to an alternate pharmaceutical storage location, where it places the bottled prescription drug for storage until it is retrieved by the customer for whom it is prescribed.

When the customer arrives with his/her prescription and successfully completes every level of verification and the barcode of the drug has been successfully scanned as well. The robot then retrieves the drug as follows. The robot finds the shortest distance to the alternate pharmaceutical storage location in which the drug is stored, and then uses SLAM to maneuver to said location. Then, using built-in memory systems and barcode scanners, the robot locates the prescribed pill bottle, and then uses its arm to retrieve the pill bottle. The robot returns to the customer and, using SLAM to maneuver back, gives the prescription drug pill bottle to the customer at a counter, through a window, or via an ATM.

Alternatively, when a drug requested in not in stock, and the robot has ordered a drug-creation from the nearest in-network pharmacy, and after the drug has been ordered, created, and sent to the pharmaceutical automation. In this case, the robot scans the drug (a barcode would be attached to the drug package before it is sent to the automaton from the pharmacy), and uses the in-network database to determine the flavor and nature of the drug. The robot uses its inbuilt mapping systems to locate the different drug dispensers throughout the main drug storage room, and locates the section of the room with drugs of closest relation to the drug delivered (by name, by flavor, by nature, by side-effects, etc.). The robot finds the shortest distance to the location determined, and uses SLAM to move there. The robot then uses its arm to fill one of the drug dispensers with the delivered prescription drug. Finally, the robot reports the availability of the prescription drug to the pharmacy and all its in-network doctors.

In one embodiment, the robot could use Simultaneous Localization and Mapping (SLAM). The Robot Operating System, or ROS (a robot software geared towards Linux systems for open source collaboration of robotic software), contains multiple SLAM, or Simultaneous Localization and Mapping, implementations. After doing some experiments, data that was presented showed that Gmapping, an implementation of SLAM, is far more accurate than other mapping algorithms such as Dead Reckoning, a mapping method in navigation that calculates current position by using a previously determined position. With mobile robots, the position is determined by rotary wheel encoders. The main problem that arises with a two wheel drive train is that the robot's wheels tend to frequently slip or skid, especially during turning, causing the encoders to return larger values than what they should. When encoder data is mapped, it is quite inaccurate, as no measures are taken to properly correct the slips and skids that have occurred. Using dead reckoning can lead to disasters in the pharmacy, as robots may go to wrong drug dispenser by mistake. On the other hand, SLAM builds a map whilst in an unknown environment and keeps track of the current position. Rotary encoders are used to keep track of the current location and laser scans from a laser measurement technology device made by SICK are used to correct the map when the wheels slip or skid. The laser measurement technology device can be used for a wide range of applications. The device, which detects both 2D and multi-dimensional contour data, can process information either externally or in the sensor itself. Since the encoders and the laser measurement device are working in unison, they are configured to create a more accurate map. SLAM was proven to be far more accurate after our experimentation.

ROBOT SECURITY ARCHITECTURE (FIG. 6)

Figure 6:
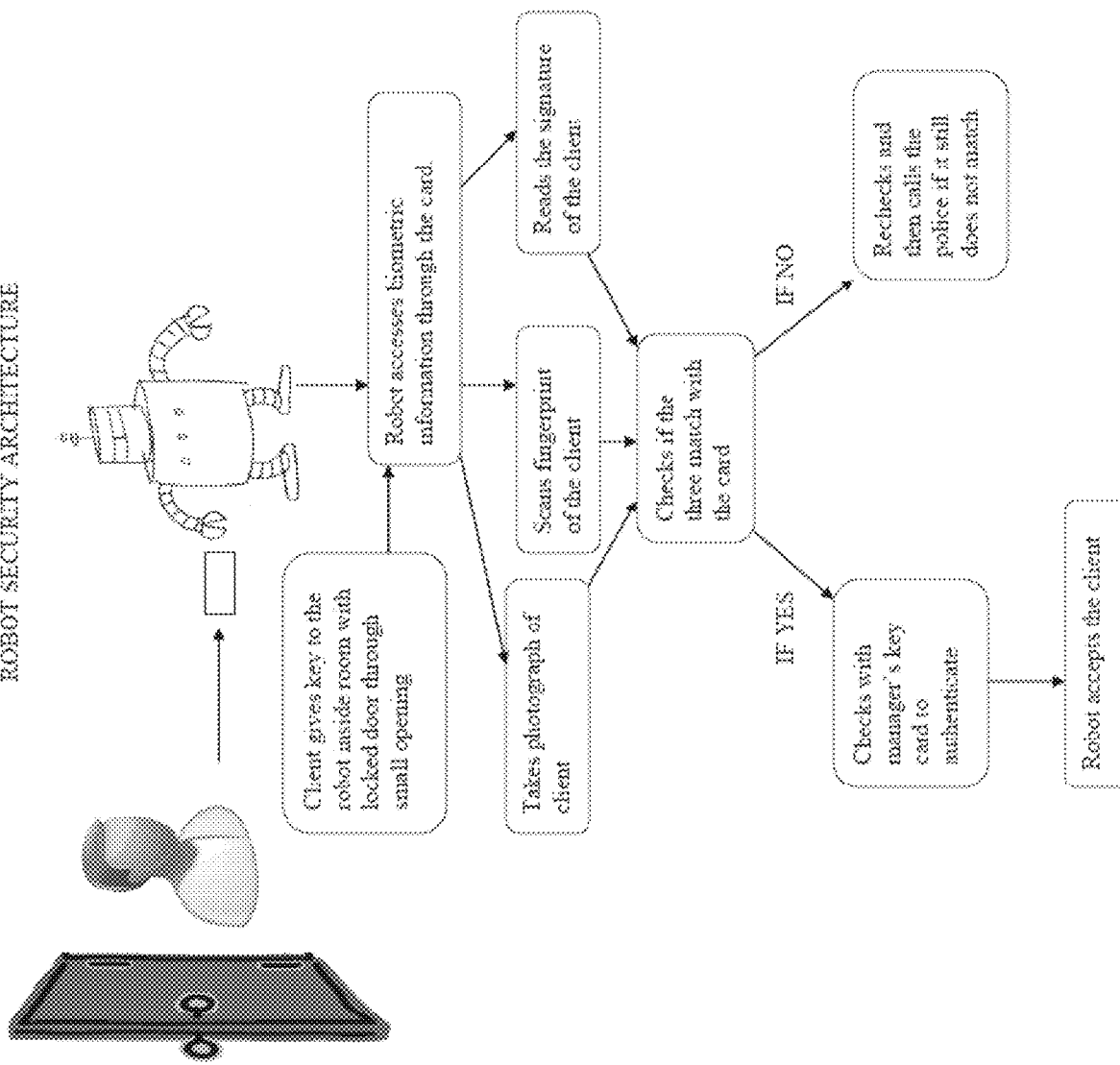
FIG. 6—Robot security architecture and biometric identification.

The robot security architecture to prevent theft or to avoid dispensing the wrong medication could include biometric scanning. The biometric scanning that could take place could be similar to that explained in U.S. Pat. No. 7,970,678, which is incorporated herein in its entirety by reference, discloses several biometric financial transaction systems and methods. For example, consumers (e.g. patients) could access their medication from a pharmacy after validation and verification of the customer by biometrics as shown in FIG. 6. Similarly, there is at least one robot that is able to fulfill orders from the consumer. A biometric or a biometric sample is any unique human characteristic of which a scan or image is taken directly from the person. The biometric or biometric sample may be, but is not limited to, any of the following: a fingerprint, a retinal image, an iris image, a facial image, and voice print.

A robot provides the ability to accept biometric and other data as input, to identify the consumer from this data, and to either complete item retrieval. Communication links exist or can be established between the robot and the database. In one embodiment, one could use a proxy to retrieve goods from the pharmacy while the patient could be remote, for example in a hospital. In this case, there could be double authentication of both the proxy and the patient. A communication link with the remote patient can be a permanent connection (e.g., a leased line), a temporary switched-circuit connection (e.g., a dialup telephone call), or a virtual connection (e.g., via packet switching). Encryption can be employed on all communication links to protect sensitive data, as is standard in the industry.

The robot may or may not be required to contain m memory any data which is personalized to or unique to the consumer in order for the consumer retrieve or deposit goods. Additionally, it can be used as a biometric input device using the consumer's voice as a biometric. A wireless or cellular telephone with a built-in finger image scanner or other biometric sensor can also be used. This is like the example above, but uses a biometric other than voice, e.g., a finger image. In addition, the consumer can use a wireless personal digital assistant (PDA) such as a smart phone, with a microphone or other biometric sensor. The wireless PDA can be used to enter and communicate an order to a robot, and a microphone or other biometric sensor can be used to input a biometric. Other access devices could be apparent to those of ordinary skill in the art.

Every medical card could include an identification (ID) code. This ID code is unique to a patient. Examples of ID codes include a digital certificate that includes the age and sex of the patient, social security number, etc.

A database can be a single computer that or a large collection of computers that serves a number of different robots. The database accepts queries of biometric data and identifies consumers from this data. Once identified, the robot retrieves goods from the consumer's medication dispenser. This information could be recorded.

In another embodiment, a wireless PDA is the access device used. As discussed above, there could be different biometrics. For illustrative purposes, a voice biometric could be used in this embodiment. Use of the system in this embodiment proceeds as follows: (1) A consumer uses the access device (wireless PDA) to contact the robot or pharmacy. (2) The robot receives the ID code from the key. In this embodiment, this could be digital certificate identification or a number stored in the device. As described above, a voice biometric is used for illustrative purposes in this embodiment, but other biometric identifiers are possible. If the consumer cannot be identified after repeated tries, the robot alerts a human customer service assistant, or security personnel, who can use other means to identify the consumer. (3) In the event of a successful identification, the robot retrieves goods for the consumer.

There are many advantages of having biometric identification. First, because each transaction is authorized using a biometric received from the consumer's person, the transaction cannot be repudiated. Second, the embodiments are convenient for the consumer, particularly located remotely from the robot, for example an elderly person in a hospital, in that the robot handles all account information, eliminating the need to recite or otherwise enter credit card or other account numbers into a telephone or PDA. Third, the use of biometrics and encryption provides security, eliminating the possibility of fraud via intercepting transmissions from the telephone or PDA. Fourth, the system supports the use of multiple consumers to access the vault simultaneously in privacy, providing flexibility for the consumer.

Although the embodiments have been described with respect to a particular biometric electronic transaction system and method for its use, it could be appreciated that various modifications of the system and method are possible without departing from the invention. All of the above mentioned ideas based on mapping using SLAM could be replaced with a similar set-up with a radio, ultrasound, light, laser, infrared, other signals, or vision based localization method.

ROBOTIC DELIVERY SYSTEM

Currently, prescription medication is not delivered to the client. There are a variety of barriers that prevent a successful delivery system to be set in place including gathering information for a secure delivery location and methods to transport the medications in a secure manner. An embodiment relates to a method for delivery of a good, comprising gathering information regarding a time and location for delivery of the good and mode of pick-up, creating a matrix of all delivery locations and modes of pick-up for each location, verifying each mode as a safe and secure pick-up mode, and delivering the good. The good could be a prescription medication. An embodiment could relate to an effective system that can be used for delivery of prescription medication.

For example, a multi-step delivery process system could be used. One step of the delivery system is gathering information regarding the optimal time and location for delivery of the client's medication, as well as the best method to pick-up the drug (called "mode of pick-up"). Another step of the delivery system is creating a matrix of all the client's delivery locations and modes of pick-up for each location. Each of these modes has to be verified as a safe and secure pick-up mode. Yet another step of delivery is the actual physical delivery of the medicine. The medicine is placed in a protective case, especially made for the delivery process.

Figure 7:
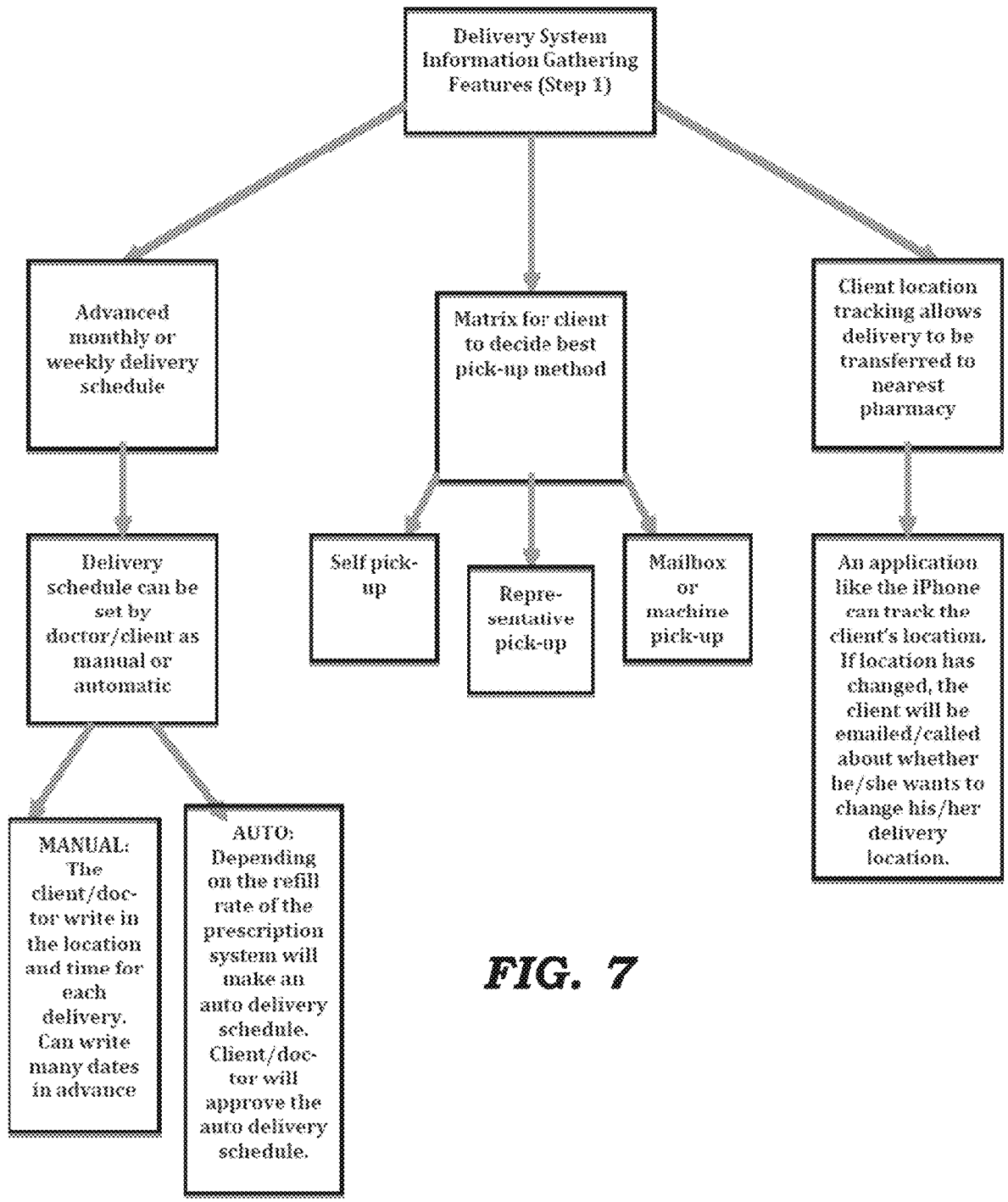
FIG. 7—Architecture of a delivery system for goods such as medication.

The step of the delivery system is gathering basic information. First, an advanced monthly or weekly delivery schedule is made for the client. This delivery schedule can be created manually by the doctor/client during the checkup via the same online database used for creating the prescription. On the other hand, the robot can create the schedule automatically. If the delivery schedule is created manually, the doctor/client will write the time (month, day, and time during that day), prescription information, and the delivery location for each of their deliveries themselves. What is especially useful for patients with a chronic illness requiring a constant dosage of prescription drugs is an automatic robotically created schedule. Here, depending on the refill rate of a prescription, the robot will automatically schedule deliveries. The robot will also automatically enter the "standard" time and location for each of these deliveries. The "standard" time and location for deliveries is a standard location and time that the client sets and can always change. For example, one can make a weekday night at the permanent place of residence the "standard" time and location. The schedule of deliveries will always be emailed 2 weeks in advance to the client and the medications will only be delivered once the client and doctor have approved information entered. Of course, there are various factors that can be adjusted. Another interesting feature in the information gathering stage is that an application on a smart phone or any other tracking device can track the client's location (only if the client wants to activate this feature). If the client is seen to be located far from the original delivery location around the time of delivery, then the client will be emailed/called about whether he/she wants to change his/her delivery location. The last aspect of the information gathering step is finding out what mode(s) of pick-up the client wants at each of the locations the client has entered into the system The three modes of pick-up are self pick-up, representative pick-up, and mailbox/machine pick-up (FIG. 7).

Using the different modes of pick-up that are entered for each of the client's specified delivery locations a matrix is created organizing all this information. The creation of the matrix and the verification process constitute as the second step (FIG. 8). Once a matrix has been created, each of the modes of pick-up is verified as authentic. Without this verification, no medication delivery will take place through that mode. This is essential because the pharmacy has the responsibility to deliver the medications securely to the client. The following will detail how the verification process will work for each of the modes. When the client adds a mode, the system will make the client sign an agreement contract that states that once the medications have been delivered to the assigned mode of pick-up, the pharmacy's responsibility is over. It is then the responsibility of the mode of pick-up to get the medications to the client. A contract will also be signed between the modes of pick-up and the pharmacy stating that the mode of pick-up has agreed to take the responsibility of delivering the medicine to the client. The contract will also state that the mode of pick-up will give the medications only to the client and nobody else. Thus, the modes of pick-up are legally responsible. All of this applies mostly only to the representative mode of pick-up. For the mailbox pick-up, the client could get the mailbox authorized as safe and secure. This function could be done by an authority or administrative agency designated and authorized to make such authorization. The client also has to sign a contract stating that they will not share the secure information of the mailbox with other people. And for the self-pick, the client simply has to sign a contract stating that they will not share the medications with others.

Once the initial information regarding the mode of pick-up is established and the contacts are signed, the verification process will begin. There are multiple methods for the verification process to take place. Here both a legal and biometric process could be used. For a legal check, the criminal records of both the client and other parties (those in the representative pick-up) will be checked. This ensures that the people handling the medications are trustworthy individuals. Other legal security measure may include past medical history of the client and other parties. Biometric security measures could also be used. Information will be collected about the client and other parties (those in the representative pick-up). Biometric information will be used to then verify that at the time of each delivery, the pick-up person is the same person that was previously verified (it will be used to match identity). Some biometric measures include: fingerprint, pupil analysis, DNA testing, among others. Additionally, the pick-up person's heart rate can be measured to check his/her nervousness. All this information will be taken to verify a "standard" time and location, before any delivery actually occurs. Once the mode of pick-up has been verified, the mode will receive a "pick-up medical card" for specific client. This "pick-up medical card" will contain a barcode that is specific to the client. For the mailbox pick-up, this medical card will be taped to the inside of the mailbox. Using this method of verification, subsequent deliveries can be automated by the robot by the use of just the "pick-up medical card."

Figure 9:
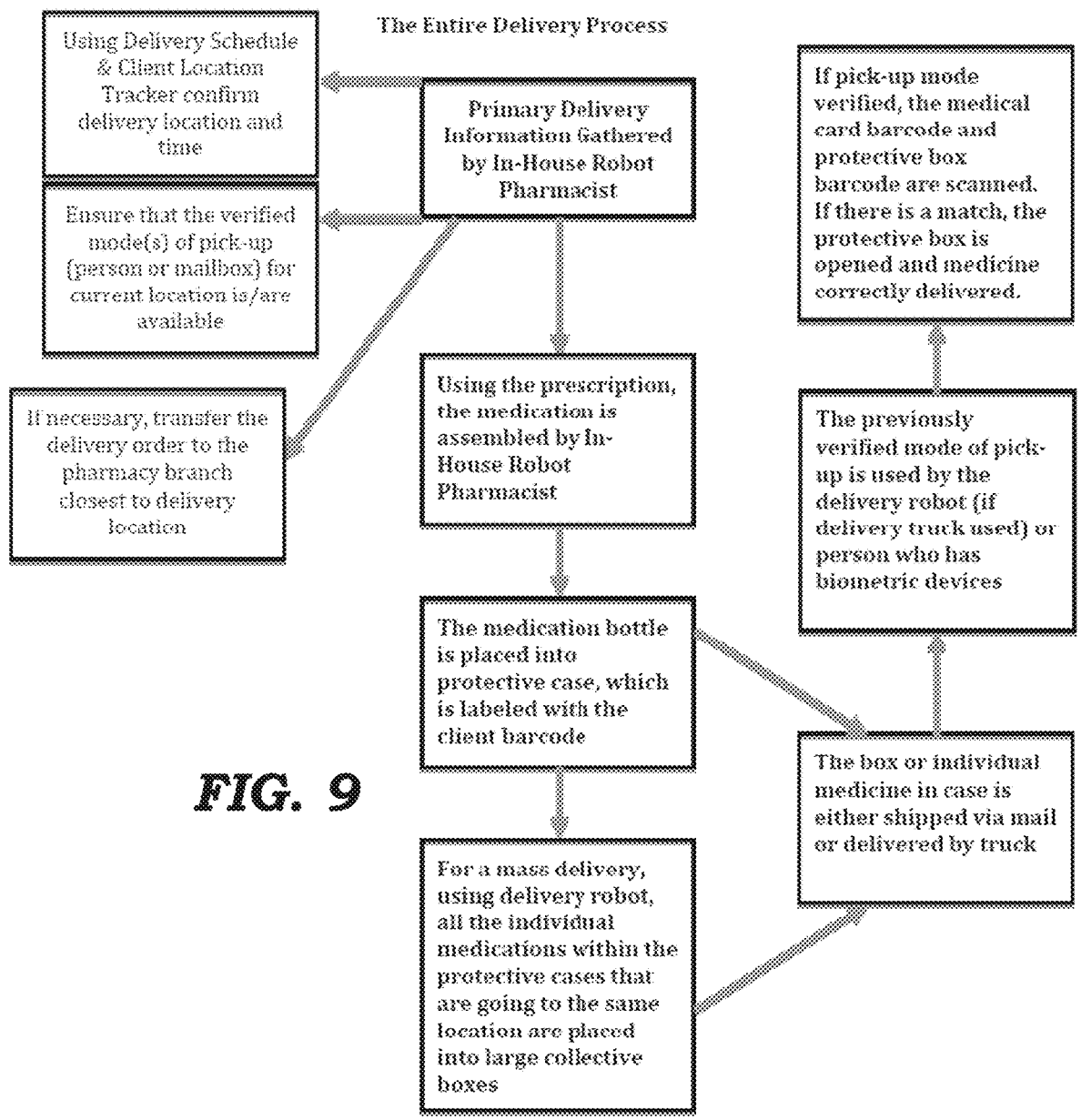
FIG. 9—Architecture of an entire delivery process system for delivery of medication.

Once the verification process for all the modes of pick-up are established, the actual delivery process can occur. The prescription is assembled by the in-house robot pharmacist. The medication bottle in then placed into a protective case, which is labeled with the client's barcode. If the protective case is tampered with then the medications will automatically be destroyed by the addition of antifreeze (ethylene glycol), for example. If multiple medications are going to the same location (for a mass delivery) then the robot will place all the medications going in the same location into one collective box. An example of a mass delivery is when multiple medications are all being delivered to an old age home, nursing home, rehabilitation center, etc. Either the individual medicine in the protective case or multiple medications in their respective protective cases within a collective box are then delivered. The delivery can take place through the mail or a truck. If the pharmacy has its own truck, then a robot can be kept in the back of the truck managing the medications. Once the medications have reached the delivery location, the correct mode of pick-up could arrive. If the biometric analysis shows a match and verifies that the pick-up mode is correct, then the pick-up mode is asked to show the "pick-up medical card." For the mailbox, the mailbox is matched and verified is the mailbox can be opened with the given password and specific key. The medical card will be inside the mailbox. Then the barcode on the "pick-up medical card" and on the protective case are scanned. If there is a match, then the protective case is opened and the medications are given to the mode of pick-up (FIG. 9).

EXAMPLES

Materials and Hardware

This project used the P3DX robot from AdeptRobots, but other similar robots could be analyzed the same way. On top of the robot could be some sort of distance sensor, which could be either a lidar or a depth sensor like the Microsoft Kinect. For this project we used the LMS lXX lidar from SICK. An Ubuntu or other Linux based laptop is mounted to the robot, and could be running ROS. A joystick is needed for teleoperation of the robot. The robot should have the tires tested in between trials, to ensure that the pressure doesn't change and cause tire variations across tests.

Software

The laptop needs a recent vers10n of ROS. This project used the Diamondback distribution, but can also be done with the Electric distribution. The laptop could also need either a premade ROS wrapper stack (ROS packages) or a custom-made one. The same applies to the lidar sensor. In this project, the P2OS stack and LMSlxx stacks were used for the robot and the laser respectively. We used Matlab as a basic visualization tool for the Dead Reckoning map.

Methods

Mapping evaluation has so far been done by checking the map of a mapping algorithm against the ground truth map of the area. This project splits mapping into 5 main areas, each with their own separate procedure and data values, which are described below.

The 90 Degrees Test: In this test, while the laptop is recording the laser and odometry data, the robot passes by a 90 degree corner of a room from approximately 2 ft away from the corner, going towards the right wall, turning and heading towards the left wall. The data collected during the test is then set to run through Gmapping stack and displayed in ROS's visualization stack, RVIZ, and directly without preprocessing to Matlab to make the Dead-Reckoning map. The maps are then checked for the angle of the corner and the number of corners that are created.

The 90 Degrees Twice Test: The procedure for this test starts the same as the previous test, but after the robot finishes its movement, it turns toward right and goes forward, turns left and goes forward again, which leaves the robot extremely close the corner. The data is again sent to Gmapping and RVIZ, and Matlab, and the maps are checked for the angle of the corner and the number of corners that are created by the map.

The Straight Away Test: In this test, the robot drives 430 cm The recorded data is then run through Gmapping and RVIZ, and Matlab, and the generated map is then checked to see how far robot reported that it has moved. The distance can be easily counted through the labeled axis, where in Matlab the units are millimeters and in RVIZ the units are 0.5 meters.

The Circle Test: In this test, the robot could move in a predetermined path that curves around obstacles, and then returns to the starting location. The data is then made into maps, and the map is checked to see how far the end location is away from the start. There could always be some distance because the robot uses skid-turning, but the distances could be measured and compared.

The Straight Wall Test: In this test, the robot could start at the beginning of a long wall. It could then move in a semi random pattern of left and right that lead towards the end of the wall, with the robot ending against the wall at the very end. The data is then made into a map, and then checked to see how straight the wall is. Since at the beginning and the end the robot is against the wall, a line drawn between the two is where the wall should be, and then the wall visible is compared against the real wall.

Results

To ensure that all results were accurate, each of the five tests was done five times for both SLAM and Dead Reckoning.

The 90 Degree Test: In the 90 Degrees Test, SLAM performed far better, as only one angle was produced on the map, and the average of the angles from the five trials was 91.8°, which has only 2% error, as seen in Table 1. However, Dead Reckoning produced two or three separate angles on the map, although they were only 10 cm away from each other and appear as one when the map is zoomed out. To deal with this problem, both or all three of the angles produced by Dead Reckoning in one trial were averaged to find a final angle measurement of the trial. The average of those five final measurements showed that Dead Reckoning displayed and angle of approximately 98.5°, which has 9.4% error. The standard deviation for the SLAM trials was 0.84 degrees, while for the Dead Reckoning trials it was 0.97 degrees, showing increased consistency in the trials done by SLAM on ROS. Table 1 is a data table of the test showing the angles from both SLAM and Dead Reckoning:

TABLE 1

Data from Dead Reckoning and SLAM of mapping a 90 degree corner.

| 90 Degree Test Trial No | Dead Reckoning Number of Angles | Angle Measures | Average of Angles | SLAM Number of Angles | Angle Measures | Average of Angles |
|---|---|---|---|---|---|---|
| 1.0 | 3.0 | 101, 95, 97 | 97.6 | 1.0 | 92.0 | 92.0 |
| 2.0 | 3.0 | 94, 105, 99 | 99.3 | 1.0 | 93.0 | 93.0 |
| 3.0 | 2.0 | 98, 99 | 98.5 | 1.0 | 91.0 | 91.0 |
| 4.0 | 3.0 | 101, 92, 99 | 97.3 | 1.0 | 91.0 | 91.0 |
| 5.0 | 2.0 | 96,103 | 99.5 | 1.0 | 92.0 | 92.0 |
| Average | 2.6 | | 98.4 | 1.0 | | 91.8 |
| Standard Deviation | | | 0.969 | | | 0.836 |

The 90 Degree Twice Test: The next test performed was the 90 Degrees Twice Test. This test was controversial, because 2 or 3 angles were created in each trial for both SLAM and Dead Reckoning. So, Dead Reckoning created about the same number of angles it did in the 90 Degrees Test, and SLAM created many more than the previous test because the area was scanned twice. SLAM showed two completely separate walls, while Dead Reckoning showed three angles near each other like the last test. However, SLAM was still more accurate in the angle of the wall than Dead Reckoning; the average of all the angles in SLAM was 93.3°, which has an error of 3.7%, and in Dead Reckoning the average was 110.6°, which has an error of 22.8%, as seen in Table 2. Although multiple angles were created in both, Dead Reckoning was not able to measure the angle correctly. In Dead Reckoning, the standard deviation was 2.05 degrees, while in SLAM it was 0.63 degrees, again showing that results in SLAM are more precise. Table 2 is a data table of the second test from both SLAM and Dead Reckoning:

TABLE 2

Dead Reckoning and SLAM mapping a 90 degree angle.

| 90 Degrees Twice Test Trial No | Dead Reckoning Number of Angles | Angle Measures | Average of Angles | SLAM Number of Angles | Angle Measures | Average of Angles |
|---|---|---|---|---|---|---|
| 1.0 | 3.0 | 112, 115, 110 | 112.3 | 2.0 | 93, 95 | 94.0 |
| 2.0 | 2.0 | 109, 111 | 110.0 | 2.0 | 94, 93 | 93.5 |
| 3.0 | 3.0 | 108, 110, 111 | 109.6 | 3.0 | 94, 91, 92 | 92.3 |
| 4.0 | 3.0 | 107, 108, 109 | 108.0 | 2.0 | 92, 94 | 93.0 |
| 5.0 | 2.0 | 112, 114 | 113.0 | 2.0 | 91, 96 | 93.5 |
| Average | 2.6 | | 110.6 | 2.2 | | 93.3 |
| Standard Deviation | | | 2.048 | | | 0.630 |

The Straight Away Test: In the five Dead Reckoning trials, when the actual distance was 4.3 meters, the average distance travelled by the robot was 4.58 meters, as seen in Table 3. The distance displayed on the Dead Reckoning map was on average 0.28 meters off the true distance. SLAM displayed a far more accurate distance, with an average of 4.18 meters. The ROS software was off by an average of 0.12 meters, less than half the inaccuracy presented by Dead Reckoning. The standard deviation of the five Dead Reckoning trials was 0.125 meters, while the deviation for the SLAM trials was only 0.1 meters. Table 3 is a data table for this Straight Away Test of the 4.3 meter run. The units on the Dead Reckoning map are in millimeters and the ROS map has squares that are each 0.5 meters squared:

TABLE 3

Dead Reckoning and SLAM mapping while moving 4.3 meters.

| Straight Away Test Trial No | Dead Reckoning Distance | How Far Off | SLAM Distance | How Far Off |
|---|---|---|---|---|
| 1.0 | 4.4 | 0.6 | 4.1 | 0.2 |
| 2.0 | 4.6 | 0.3 | 4.2 | 0.1 |
| 3.0 | 4.6 | 0.3 | 4.0 | 0.3 |
| 4.0 | 4.7 | 0.4 | 4.4 | 0.1 |
| 5.0 | 4.6 | 0.3 | 4.3 | 0.0 |
| Average | 4.6 | 0.3 | 4.2 | 0.1 |
| Standard Deviation | | 0.125 | | 0.100 |

The Circle Test: Circle Test also assessed the rotary encoder problem in the Dead Reckoning software, as the P3-DX had to go around an obstacle in the center of the room and arrive back in the exact same spot. The initial and final locations of the robot should have been the same. However, because of the wheels' skidding on the robot, the Dead Reckoning map showed that the robot did not end in the same location. The average of the distances from the start on Dead Reckoning was 1.05 meters, while the average for SLAM was 0.58 meters, as seen in Table 4. This was only test where the standard deviation of SLAM, 0.28 meters, was greater than that of Dead Reckoning, being 0.17 meters.

TABLE 4

Dead Reckoning and SLAM mapping while traveling in a circle. The circle was then checked to see how far the robot was off in its ending point.

| Circle Test Trial No | Dead Reckoning Distance From Start | SLAM Distance From Start |
|---|---|---|
| 1.0 | 0.9 | 0.6 |
| 2.0 | 1.1 | 0.5 |
| 3.0 | 1.2 | 0.2 |
| 4.0 | 0.9 | 1.0 |
| 5.0 | 1.2 | 0.6 |
| Average | 1.1 | 0.6 |
| Standard Deviation | 0.166 | 0.284 |

The Straight Wall Test: The final test, the Straight Wall Test, was done to see whether or not Dead Reckoning and SLAM could accurately locate a wall even if the P3-DX was swaying wildly left and right. In this test, SLAM displayed a much more accurate map, as it only showed one wall, while Dead Reckoning showed a map that did not present a definite location of the wall. To evaluate this test, a line was placed where the wall actually should have been on the map, and the various distances from the line were measured at set intervals. For each trial, the average of these distances was taken, as seen in Table 5. The average of all trials for Dead Reckoning was 1.07 meters, which is large in comparison to the 0.19 meters for SLAM. Dead Reckoning was also much less precise, because the standard deviation of its trials was 0.31 meters, in comparison to SLAM's 0.04 meters. Table 5 is a data table for the test:

TABLE 5

Dead Reckoning and SLAM mapping a straight wall.

| Straight Wall Test Trial No | Dead Reckoning Average Distance From Wall | SLAM Average Distance From Wall |
|---|---|---|
| 1 | 1.26 | 0.17 |
| 2 | 1.13 | 0.21 |
| 3 | 0.96 | 0.14 |
| 4 | 0.60 | 0.19 |
| 5 | 1.40 | 0.23 |
| Average | 1.07 | 0.19 |
| Standard Deviation | 0.308 | 0.036 |

Discussion

90 Degree Test: The Dead Reckoning map had either two or three angles that formed corners, but their separation was minuscule and only visible if the corner was focused on. Of all the trials, the average was 98.4° with a standard deviation of 0.969 degrees. For the SLAM map, there was only one corner, and the average of all of its trials gets an average of 91.8° with a standard deviation of 0.836 degrees. Since the Dead Reckoning map had multiple walls, it can be concluded that the robot had slipped twice, causing the two extra, but very close and similar, walls. The SLAM method, with its slipping correction, does not run into the same problem with the multiple walls. SLAM also fixes the skidding which happens during the turning, making the angles more accurate, which in this test was 466% more accurate from the formula $100*(Ø-Ødr)/(Ø-Ør)$, where Ø is 90°, Ødr is the angle from Dead Reckoning, and Ør is the angle from SLAM. Since the standard deviation for both methods are small, it shows that the values are consistent, which in the case of Dead Reckoning means consistently off, and in the case of SLAM mean consistently accurate.

90 Degree Twice Test: In this test, just like the prior one, the Dead Reckoning map had either two or three walls, all very close and similar in angle. But with this test the SLAM also has multiple walls, except that the walls are entirely separate, with a large distance between them This happened because of the way that SLAM works; SLAM tries to match points from what it saw in the past to the current scans to try to fix the odometry skids and slips. This encounters problems when the robot is in a rapidly changing environment, such as a dynamic environment, or one which the robot is really close to a wall, where all small turns seem extreme. The program then sometimes mismatches what the robot thinks is the same point, and then moves its location to match where it would be if the points actually did match. This causes the completely different walls when the laser data gets mapped from the new location. Even so, the average of all of the corners for SLAM is still close to 90 with an average of 93.26 with a standard deviation of 0.6304 degrees. Dead Reckoning also got a worse than the previous test with more turns that the robot skids on, with an average of 101.6 with a standard deviation of 2.048 degrees. Using the formula from the last test, we get that SLAM is 355% better in its angle, but because of having separate walls unlike Dead Reckoning, which has very close walls together, it is not as accurate of a map. Since the standard deviations for the data sets are small, it shows that the data is consistent.

The Straight Away Test: In this test, the distance travelled is measured and then compared relative to what it should be, 4.3 meters. The reason this test would reveal different results from Dead Reckoning to SLAM is that with Dead Reckoning, when the wheels slip, the robot thinks that it has moved forward while it had not actually moved during that time. With SLAM, it should report something in the distance with the distance sensor, and adjust its location based on matching those objects to where it saw them in the past, making slip less effective in changing how far the robot thinks it has gone. For Dead Reckoning, it has an average of 0.28 meters more than 4.3 meters with a standard deviation of 0.125 meters, and with SLAM, it has an average of 0.118 meters less than 4.3 meters with a standard deviation of 0.1001 meters. The SLAM algorithm is 237% better than Dead Reckoning, but both are really accurate numbers. For both Dead Reckoning and SLAM have the standard deviation relatively high, meaning that even though they are both relatively good numbers, it is not consistent.

The Circle Test: When the robot tries to turn, since it has two wheels, it skids to turn. This test tries to see if the robot, while it is skidding in the same direction on a circular path, can keep its odometry accurate. With Dead Reckoning, the average distance away from the start location is 1.05 meters with a standard deviation of 0.168 meters while SLAM has an average of 0.58 meters and a standard deviation of 0.286 meters. Since the standard deviation for Dead Reckoning is small, it shows that it is consistently off, while SLAM has a relatively high standard deviation, meaning that although it can be really accurate, it is not precise all the time. This shows that SLAM is 180% better at keeping the skidding moderated and ending up in the same place as it started on the map. Since this test has the robot skidding the entire time, and all of the skidding occurs during a clockwise turn, all of the errors are being accumulated the fastest out of all the tests. SLAM's ability to use laser scans to correct its position is more apparent in this test.

The Straight Wall Test: This test sees how well the robot keeps its odometry together as it skids in opposite directions. For SLAM, only one distinct wall is produced on the map. On the Dead Reckoning map, there are many walls visualized, but for the sake of analyzing, we could be just looking at the actual wall and the wall farthest from the actual wall. By comparing the farthest wall to the actual wall (which can be done by placing a line between the end and beginning of the robot's path, where it was against the wall), we get the accuracy of the generated wall. This test had the skidding in opposite directions. In the case of Dead Reckoning, it does not show one inaccurate map, but multiple walls placed atop each other. SLAM manages to keep the robot's position accurate, preventing multiple walls from being displayed. For each map, an average of the distance between the displayed wall and the actual wall was recorded, and overall, the average of those averages for the Dead Reckoning map are 1.07 meters away from the wall with a standard deviation of 0.308 meters, while SLAM has an average of 0.187 meters away with a standard deviation of 0.035 meters. Since the standard deviation for both of these figures are small, it shows that these values are consistently away for the Dead Reckoning and consistently good for SLAM. This shows that SLAM is 572% better at keeping the wall where it should be when it is put into a constant skidding environment.

This work is unique from other published findings because unlike other map evaluation methods, this project compares each part of mapping independently, while other methods compare the map in whole. Our results were also unique in that they quantitatively proved a fatal flaw in SLAM, allowing for more improvement of the SLAM algorithm by understanding which portions of the algorithm needs improvement, and in turn, allows programmers to be more direct in fixing problems that show up.

This project also allows for less strict testing environments, whereas before, a carefully and tediously measured map of the room being tested in has to be made. On the contrary, we have now created a standard testing environment for map-making algorithms, which can easily be reconstructed. In almost any environment, one can slightly change their perimeters to match the standard testing area and complete all five tests, and evaluated their own algorithms.

After conducting this project, one can see that Simultaneous Localization and Mapping, or SLAM, is a more effective method of mapping than Dead Reckoning. Using laser scans to correct wheel encoder data when wheels slip and skid is an efficient way to make a more accurate map. In four out of the five tests conducted to evaluate map accuracy, SLAM performed better and displayed a better map 4 out of the 5 times. The reason SLAM did not accurately display the 90 Degrees Twice Test is because in a rapidly changing environment, SLAM's laser data incorrectly fixes the encoder data, creating two different images of one object. This is the one major error in SLAM, which could be assessed in a future project. These results support the hypothesis because they do prove that SLAM is a better method of mapping than Dead Reckoning. With ROS and SLAM technology, pharmacy automation could be made easier and more helpful to humans.

What is claimed is:

1. A pharmacy automation system comprising a robot, the robot configured to:

receive a prescription comprising information of a prescribed medication;

determine a location of the prescribed medication using an internal mapping;

fill a container with the prescribed medication when the prescribed medication is available in a pharmacy;

verify authenticity of one of a patient and a proxy upon arrival to pick up the prescribed medication by checking and approving an identification of the one of the patient and the proxy; and retrieve the container and hand over the container with the prescribed medication to one of the patient and the proxy;

wherein the internal mapping is done by the robot and wherein the internal mapping comprises determining a shortest distance between the patient and the prescribed medication or a shortest distance between the proxy and the prescribed medication.

2. The pharmacy automation system of claim 1, wherein the prescription is in a form of one of an audio and a digital recording.

3. The pharmacy automation system of claim 1, wherein the prescription is in a form of an internet protocol (IP) address card.

4. The pharmacy automation system of claim 1, wherein if the prescribed medication is not available in the pharmacy, the robot is configured to order a drug from a nearest pharmacy in network.

5. The pharmacy automation system of claim 1, wherein the robot comprises a hardware device and a software to perform the internal mapping, wherein the internal mapping is a simultaneous localization and mapping (SLAM).

6. The pharmacy automation system of claim 5, wherein the robot determines the prescribed medication from the prescription.

7. The pharmacy automation system of claim 6, wherein the prescription is in a form of a prescription note or a medical card comprising a built-in memory chip containing at least information regarding the prescribed medication.

8. The pharmacy automation system of claim 6, wherein the robot is further configured to upload an information of the patient and/or the proxy to a doctor directly or an intermediary, the intermediary comprising an online database containing a list of doctors or a cloud network.

9. The pharmacy automation system of claim 5, wherein the hardware device comprises a rotary encoder and a laser.

10. The pharmacy automation system of claim 5, wherein the software comprises a robot operating system.

11. The pharmacy automation system of claim 1, wherein the robot, verifying the authenticity of one of the patient and the proxy, is operable to check and approve thean identification of one of the patient and the proxy.

12. The pharmacy automation system of claim 11, wherein the identification is in a form of biometric data and/or a photograph.

13. The pharmacy automation system of claim 12, wherein the biometric data comprises one of a fingerprint, a retinal image, an iris image, a facial image, and voice print.

14. The pharmacy automation system of claim 1, wherein the robot fills the container with a request amount of the prescribed medication as per the prescription.

15. The pharmacy automation system of claim 1, wherein the robot is operable to retrieve a lid and seal the container upon filling the container with the prescribed medication.

16. The pharmacy automation system of claim 1, wherein the robot is further operable to track a current location of the patient.

17. The pharmacy automation system of claim 16, wherein the robot is further operable to maneuver to the current location of the patient.

18. The pharmacy automation system of claim 17, wherein the robot is further operable to deliver the prescribed medication at the current location of the patient.

19. The pharmacy automation system of claim 18, wherein the robot is further operable to communicate a schedule electronically to the patient in advance of time at which a delivery of the prescribed medication is to be made, wherein the schedule comprises at least a time and a location for thea delivery of the prescribed medication.

20. The pharmacy automation system of claim 19, wherein the robot is further operable to deliver the prescribed medication as per the schedule.

* * * * *